US006893816B1

(12) United States Patent
Beattie

(10) Patent No.: US 6,893,816 B1
(45) Date of Patent: May 17, 2005

(54) MICROFABRICATED, FLOWTHROUGH POROUS APPARATUS FOR DISCRETE DETECTION OF BINDING REACTIONS

(75) Inventor: Kenneth L. Beattie, The Woodlands, TX (US)

(73) Assignee: Houston Advanced Research Center, Woodlands, TX (US)

(*) Notice: Subject to any disclaimer, the term of this patent is extended or adjusted under 35 U.S.C. 154(b) by 200 days.

(21) Appl. No.: 09/063,356

(22) Filed: Apr. 21, 1998

Related U.S. Application Data

(63) Continuation of application No. 08/631,751, filed on Apr. 10, 1996, now Pat. No. 5,843,767, which is a continuation of application No. PCT/US94/12282, filed on Oct. 27, 1994, application No. 09/063,356, which is a continuation-in-part of application No. 08/141,969, filed on Oct. 28, 1993, now abandoned.

(51) Int. Cl.[7] .......................... C12Q 1/68; G01N 33/552

(52) U.S. Cl. ............................ 435/6; 422/68.1; 422/69; 435/7.1; 435/7.2; 435/7.8; 435/287.1; 435/287.2; 435/287.4; 435/970; 435/973; 436/501; 436/518; 436/527; 436/535; 436/805; 436/807; 436/808; 436/809

(58) Field of Search ................................. 435/6, 7.1, 7.2, 435/7.8, 970, 973, 287.1, 287.2, 288.4; 436/518, 527, 535, 805, 807, 808, 809, 501; 422/68.1, 69

(56) References Cited

U.S. PATENT DOCUMENTS

| | | | | |
|---|---|---|---|---|
| 4,693,985 A | * | 9/1987 | Degen et al. ................ | 436/531 |
| 4,874,691 A | * | 10/1989 | Chandler ........................ | 435/7 |
| 4,888,414 A | * | 12/1989 | Knutson | |
| 4,916,056 A | * | 4/1990 | Brown, III et al. ............. | 435/7 |
| 5,077,210 A | | 12/1991 | Eigler et al. ................. | 435/176 |
| 5,143,854 A | | 9/1992 | Pirrung et al. ............... | 436/518 |
| 5,188,733 A | | 2/1993 | Wang et al. ............ | 210/321.84 |
| 5,231,035 A | | 7/1993 | Akers, Jr. ..................... | 436/531 |
| 5,234,594 A | | 8/1993 | Tonucci et al. ......... | 210/500.26 |
| 5,244,815 A | | 9/1993 | Guirguis ...................... | 436/530 |
| 5,585,968 A | * | 12/1996 | Guhman et al. | |
| 5,677,195 A | * | 10/1997 | Winkler et al. .............. | 436/518 |
| 5,763,263 A | * | 6/1998 | Dehlinger | |
| 5,843,767 A | * | 12/1998 | Beattie ..................... | 435/287.1 |

FOREIGN PATENT DOCUMENTS

| | | |
|---|---|---|
| EP | 0 505 632 | 3/1991 |
| WO | 89/10977 | 5/1989 |

OTHER PUBLICATIONS

Kenneth Beattie et al., "Genosensor Technology," Clinical Chemistry 39:719–722 (1993).

Radoje Drmanac et al., "Sequencing by Hybridization: Towards an Automated Sequencing of one Million M1 Clones Arrayed on Membrane," Electrophoresus 13:566–573 (1992).

Mitchell D. Eggers et al., "Genosensors: Microfabricated Devices for Automated DNA Sequence Analysis," Advances in DNA Sequencing Technology 1891, Proceedings Repring, SPIE (1993).

(Continued)

*Primary Examiner*—David Saunders
(74) *Attorney, Agent, or Firm*—Blank Rome LLP

(57) ABSTRACT

An improved microfabricated apparatus for conducting a multiplicity of individual and simultaneous binding reactions is described. The apparatus comprises a substrate on which are located discrete and isolated sites for binding reactions. The apparatus is characterized by discrete and isolated regions that extend through said substrate and terminate on a second surface thereof such that when a test sample is applied to the substrate, it is capable of penetrating through each such region during the course of said binding reaction. The apparatus is especially useful for sequencing by hybridization of DNA molecules.

8 Claims, 6 Drawing Sheets

OTHER PUBLICATIONS

Sebastian Meier–Ewart et al., "An Automated Approach to Generating Expressed Sequence Catalogues," Nature 361:375–376 (1993).

K. R. Khrapko et al., "Method for DNA Sequencing by Hybridization with Oligonucleotide Matrix," J.DNA Sequencing and Mapping 1:375–388 (1991).

Gjermund Kittilsland et al., "A Sub–Micron Particle Filter in Silicon," Sensors and Actuators A21–A23 904–907 (1990).

Randall K. Saiki et al., "Genetic Analysis of Amplified DNA with Immobilized Sequence–Specific Oligonucleotode Probes," Proc. Natl. Acad. Sci USA 86:6230–6234 (1989).

E. M. Southern, "Analyzing and Comparing Nucleic Acid Sequences by Hybridization to Arrays of Oligonucleotides: Evaluation Using Experimental Models," Genomics 13:1008–1017 (1992).

R. J. Tonucci et al., "Nanochannel Array Glass," Science 258:783–785 (1992).

Dialog abstract of European patent document 0 347 579 (listed above as document A9), Derwent World Patents Index accession No. 90–001005/01.

Dialog abstract of Fed. Rep. of Germanu patent documents 38 01 987 (listed above as document A11), Derwent World Patents Index accession No. 89–221475/31.

Drmanac, R. et al., "DNA Sequence Determination by Hybridization: A Strategy for Efficient Large–Scale Sequencing," *Science* 260:1649–1652 (1993).

\* cited by examiner-

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
      (A) LENGTH: 130 base pairs
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO: 1:

GCAAGCTTGC TGGTGAAAAG GACCTCTCGA AGTGTTGGAT ATAGGCCAGA CTTTGTTGGA      60

TTTGAAATTC CAGACAAGTT TGTTGTTGGA TATGCCCTTG ACTATAATGA GTACTTCAGG     120

GATTTGAATC                                                           130

(2) INFORMATION FOR SEQ ID NO: 2:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: hamster, human and mouse (xi) SEQUENCE DESCRIPTION: SEQ ID NO: 2:

AACAGCTTGC TGGTGAAAAG GACCYCTMGA AGTGTTGGAT AYARGCCAGA CTGTAAG        57

(2) INFORMATION FOR SEQ ID NO: 3:

(i) SEQUENCE CHARACTERISTICS:
        (A) LENGTH: 47 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: CHO cells (xi) SEQUENCE DESCRIPTION: SEQ ID NO: 3:

AACAGCTTGC TGGTGAAAAG GACCTCTCAT ATAGGCCAGA CTGTAAG                   47

(2) INFORMATION FOR SEQ ID NO: 4:

(i) SEQUENCE CHARACTERISTICS:
        (A) LENGTH: 87 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: hamster, human and mouse (xi) SEQUENCE DESCRIPTION: SEQ ID NO: 4:

TACAGTTGTT GGATTTGAAA TTCCAGACAA GTTTGTTGTW GGATATGCCC TTGACTATAA      60

TGARTACTTC AGGRATTTGA ATGTAAT                                         87

(2) INFORMATION FOR SEQ ID NO: 5:

(i) SEQUENCE CHARACTERISTICS:
        (A) LENGTH: 87 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: CHO cells (xi) SEQUENCE DESCRIPTION: SEQ ID NO: 5:

TACAGTTGTT GGATTTGGAA TTCCAGCAAG TTTGTTGTTG GATATGCCCT TGACTATAAA        60

TGAGTACTTC AGGCATTTGA ATGTAAT        87

(2) INFORMATION FOR SEQ ID NO: 6:

(i) SEQUENCE CHARACTERISTICS:
        (A) LENGTH: 24 base pairs
        (B) TYPE: nucleic acid
        (C) STRANDEDNESS: both
        (D) TOPOLOGY: linear (xi) SEQUENCE DESCRIPTION: SEQ ID NO: 6:

GTTCTATTGT CTTTCCCATA TGTC        24

(2) INFORMATION FOR SEQ ID NO: 7:

(i) SEQUENCE CHARACTERISTICS:
        (A) LENGTH: 25 base pairs
        (B) TYPE: nucleic acid
        (C) STRANDEDNESS: both
        (D) TOPOLOGY: linear (xi) SEQUENCE DESCRIPTION: SEQ ID NO: 7:

TCAGTCTGGT CAAATGACGA GGTGC        25

(2) INFORMATION FOR SEQ ID NO: 8:

(i) SEQUENCE CHARACTERISTICS:
        (A) LENGTH: 24 base pairs
        (B) TYPE: nucleic acid
        (C) STRANDEDNESS: both
        (D) TOPOLOGY: linear (xi) SEQUENCE DESCRIPTION: SEQ ID NO: 8:

CTGTGATTCT TTACAGTTGT TGGA        24

(2) INFORMATION FOR SEQ ID NO: 9:

(i) SEQUENCE CHARACTERISTICS:
        (A) LENGTH: 26 base pairs
        (B) TYPE: nucleic acid
        (C) STRANDEDNESS: both
        (D) TOPOLOGY: linear (xi) SEQUENCE DESCRIPTION: SEQ ID NO: 9:

CATTAATTAC ATTCAAATCC CTGAAG        26

(2) INFORMATION FOR SEQ ID NO: 10:

(i) SEQUENCE CHARACTERISTICS:
        (A) LENGTH: 11 base pairs
        (B) TYPE: nucleic acid
        (C) STRANDEDNESS: both
        (D) TOPOLOGY: linear (xi) SEQUENCE DESCRIPTION: SEQ ID NO: 10:

ACTCATTTAT A        11

(2) INFORMATION FOR SEQ ID NO: 11:

(i) SEQUENCE CHARACTERISTICS:
        (A) LENGTH: 10 base pairs
        (B) TYPE: nucleic acid
        (C) STRANDEDNESS: both
        (D) TOPOLOGY: linear

```
        (xi) SEQUENCE DESCRIPTION: SEQ ID NO: 11:

TATATGAGAG                                                              10

(2) INFORMATION FOR SEQ ID NO: 12:

(i) SEQUENCE CHARACTERISTICS:
         (A) LENGTH: 10 base pairs
         (B) TYPE: nucleic acid
         (C) STRANDEDNESS: both
         (D) TOPOLOGY: linear (xi) SEQUENCE DESCRIPTION: SEQ ID NO: 12:

ATTCCAAATC                                                              10

(2) INFORMATION FOR SEQ ID NO: 13:

(i) SEQUENCE CHARACTERISTICS:
         (A) LENGTH: 10 base pairs
         (B) TYPE: nucleic acid
         (C) STRANDEDNESS: both
         (D) TOPOLOGY: linear (xi) SEQUENCE DESCRIPTION: SEQ ID NO: 13:

TCCAACAACT                                                              10

(2) INFORMATION FOR SEQ ID NO: 14:

(i) SEQUENCE CHARACTERISTICS:
         (A) LENGTH: 10 base pairs
         (B) TYPE: nucleic acid
         (C) STRANDEDNESS: both
         (D) TOPOLOGY: linear (xi) SEQUENCE DESCRIPTION: SEQ ID NO: 14:

ATTTCAAATC                                                              10

(2) INFORMATION FOR SEQ ID NO: 15:

(i) SEQUENCE CHARACTERISTICS:
         (A) LENGTH: 10 base pairs
         (B) TYPE: nucleic acid
         (C) STRANDEDNESS: both
         (D) TOPOLOGY: linear (xi) SEQUENCE DESCRIPTION: SEQ ID NO: 15:

ACAAACTTGT                                                              10

(2) INFORMATION FOR SEQ ID NO: 16:

(i) SEQUENCE CHARACTERISTICS:
         (A) LENGTH: 10 base pairs
         (B) TYPE: nucleic acid
         (C) STRANDEDNESS: both
         (D) TOPOLOGY: linear (xi) SEQUENCE DESCRIPTION: SEQ ID NO: 16:

ACTCATTATA                                                              10

(2) INFORMATION FOR SEQ ID NO: 17:

(i) SEQUENCE CHARACTERISTICS:
         (A) LENGTH: 11 base pairs
```

```
        (B) TYPE: nucleic acid
        (C) STRANDEDNESS: both
        (D) TOPOLOGY: linear (xi) SEQUENCE DESCRIPTION: SEQ ID NO: 17:

AATTACATTC A                                                                11
```

MICROFABRICATED, FLOWTHROUGH POROUS APPARATUS FOR DISCRETE DETECTION OF BINDING REACTIONS

This application is a continuation of application Ser. No. 08/631,751, filed Apr. 10, 1996 now U.S. Pat. No. 5,843,767 which is a continuation of PCT/US94/12282, filed Oct. 27, 1996, which is a CIP of Ser. No. PCT/US94/12282, filed Oct. 27, 1994, which is a CIP of Ser. No. 08/141,969, filed Oct. 28, 1993 abandoned.

BACKGROUND OF THE INVENTION

Several forms of arrayed hybridization reactions are currently being developed under the common rubric of "sequencing by hybridization" (SBH). Included are "format 1" versions of SBH, involving stepwise hybridization of different oligonucleotide probes with arrays of DNA samples gridded onto membranes, and "format 2" implementations. involving hybridization of a single nucleic acid "target sequence" to an array of oligonucleotide probes tethered to a flat surface or immobilized within a thin gel matrix. The term "genosensor" has heretofore referred to a form of SBH in which oligonucleotides are tethered to a surface in a two-dimensional array and serve as recognition elements for complementary sequences present in a nucleic acid "target" sequence. The genosensor concept further includes microfabricated devices in which microelectronic components are present in each test site, permitting rapid, addressable detection of hybridization across the array.

The present invention provides a novel flow-through genosensor, in which nucleic acid recognition elements are immobilized within densely packed pores or channels, arranged in patches across a wafer of solid support material. Known microfabrication techniques are available for producing microchannel or nanochannel glass and porous silicon useful as support wafers. Flow-through genosensors utilize a variety of conventional detection methods, including microfabricated optical and electronic detection components, film, charge-coupled-device arrays, camera systems and phosphor storage technology.

The following advantages for the novel flow-through apparatus herein as compared to known flat surface designs are obtained:

(1) improved detection sensitivity due to the vastly increased surface area which increases the quantity of nucleic acid bound per cross sectional area;

(2) minimization of a rate-limiting diffusion step preceding the hybridization action (reducing the time required for the average target molecule to encounter a surface-tethered probe from hours to milliseconds), speeding hybridization and enabling mismatch discrimination at both forward and reverse reactions;

(3) enablement of the analysis of dilute nucleic acid solutions because of the ability to gradually flow the solution through the porous wafer;

(4) facilitation of subsequent rounds of hybridization involving delivery of probes to specific sites within the hybridization array;

(5) facilitation of the recovery of bound nucleic acids from specific hybridization sites within the array, enabling the further analysis of such recovered molecules; and (6) facilitation of the chemical bonding of probe molecules to the surface within each isolated region due to the avoidance of the rapid drying of small droploets of probe solution on flat surfaces exposed to the atmosphere.

Accordingly, the present invention provides an improved apparatus and method
  for the simultaneous conduct of a multiplicity of binding reactions on a substrate,
  which substrate is a microfabricated device comprising a set of discrete and isolated regions on the substrate,
  such that each such discrete and isolated region corresponds to the location of one such binding reaction,
  in which each such discrete and isolated region contains an essentially homogeneous sample of a biomolecule of discrete chemical structure fixed to such bounded region,
  such that upon contact between the substrate and a sample (hereinafter, "test sample") containing one or more molecular species capable of controllably binding with one or more of the pre-determined biomolecules,
  the detection of the bounded regions in which such binding has taken place yields a pattern of binding capable of characterizing or otherwise identifying the molecular species in the test sample.

The present invention specifically provides novel high-density and ultra-high density microfabricated, porous devices for the conduction and detection of binding reactions. In particular, the present invention provides improved "genosenors" and methods for the use thereof in the identification or characterization of nucleic acid sequences through nucleic acid probe hybridization with samples containing an uncharacterized polynucleic acid, e.g., a cDNA, mRNA, recombinant DNA, polymerase chain reaction (PRC) fragments or the like, as well as other biomolecules.

During the past decade microfabrication technology has revolutionized the electronics industry and has enabled miniaturization and automation of manufacturing processes in numerous industries. The impact of microfabrication technology in biomedical research can be seen in the growing presence of microprocessor-controlled analytical instrumentation and robotics in the laboratory, which is particularly evident in laboratories engaged in high throughput genome mapping and sequencing. The Human Genome Project is a prime example of a task that whose economics would greatly benefit from microfabricated high-density and ultra-high density hybridization devices that can be broadly applied in genome mapping and sequencing.

Hybridization of membrane-immobilized DNAs with labeled DNA probes is a widely used analytical procedure in genome mapping. Robotic devices currently enable gridding of 10,000–15,000 different target DNAs onto a 12 cm×8 cm membrane. Drmanac, R., Drmanac, S., Jarvis, J. and Labat, I. 1993, in Venter, J. C. (Ed.), *Automated DNA Sequencing and Analysis Techniques*, Academic Press, in press, and Meier-Ewert, S., Maier, E., Ahmadi. A., Curtis, J. and Lehrach, H. 1993. Science 361:375–376. Hybridization of DNA probes to such filters has numerous applications in genome mapping, including generation of linearly ordered libraries, mapping of cloned genomic segments to specific chromosomes or megaYACs, cross connection of cloned sequences in cDNA and genomic libraries, etc. Recent initiatives in "sequencing by hybridization" (SBH) aim toward miniaturized, high density hybridization arrays. A serious limitation to miniaturization of hybridization arrays in membranes or on flat surfaces is the quantity of DNA present per unit cross sectional area, which (on a two-dimensional surface) is a function of the surface area. This parameter governs the yield of hybridized DNA and thus the detection sensitivity.

Genosensors, or miniaturized "DNA chips" are currently being developed in several laboratories for hybridization analysis of DNA samples. DNA chips typically employ arrays of DNA probes tethered to flat surfaces, e.g., Fodor, S. P. A., Read, J. L., Pirrung, M. C., Stryer, L., Lu, A. T. and Solas, D. 1991. Science 251:767–773, Southern, E. M., Maskos, U. and Elder, J. K. 1992. Genomics 13:1008–1017, Eggers, M. D., Hogan, M. E., Reigh, R. K., Lamture, J. B., Beattie, K. L., Hollis, M. A., Ehrlich, D. J., Kosicki, B. B., Shumaker, J. M., Varma, R. S., Burke, B. E., Murphy, A. and Rathman, D. D. 1993. Advances in DNA Sequencing Technology, SPIE Conference, Los Angeles, Calif., and Beattie, K., Eggers, M., Shumaker, J., Hogan, M., Varma, R., Lamture, J., Hollis, M., Ehrlich, D. and Rathman, D. 1993. Clin. Chem. 39:719–722, to acquire a hybridization pattern that reflects the nucleotide sequence of the target DNA. The detection limit for hybridization on flat-surface genosensors. as in membrane hybridization, is limited by the quantity of DNA that can be bound to a two dimensional area Another limitation of these prior art approaches is the fact that a flat surface design introduces a rate-limiting step in the hybridization reaction, i.e., diffusion of target molecules over relatively long distances before encountering the complementary probes on the surface. In contrast, the microfabricated apparatus according to the present invention is designed to overcome the inherent limitations in current solid phase hybridization materials, eliminating the diffusion-limited step in flat surface hybridizations and increasing the cross sectional density of DNA.

Typically microfabricated genosensor devices are characterized by a compact physical size and the density of components located therein. Known microfabricated binding devices are typically rectangular wafer-type apparatuses with a surface area of approximate one cm, e.g., 1 cm×1 cm. The bounded regions on such devices are typically present in a density of $10^2$–$10^4$ regions/cm$^2$, although the desirability of constructing apparatuses with much higher densities has been regarded as an important objective. See Eggers and Beattie, cited above, for discussion of strategies for the construction of devices with higher densities for the bounded regions.

The microfabricated apparatuses as described herein are known to be useful for a variety of analytical tasks, including nucleic acid sequence analysis by hybridization (SBH), analysis of patterns of gene expression by hybridization of cellular mRNA to an array of gene-specific probes, immunochemical analysis of protein mixtures, epitope mapping, assay of receptor-ligand interactions, and profiling of cellular populations involving binding of cell surface molecules to specific ligands or receptors imnnobilized within individual binding sites. Although nucleic acid analysis is one principal use for such an microapparatus, it is advantageously applied to a broad range of molecular binding reactions involving small molecules, macromolecules, particles, and cellular systems. See, for example, the uses described in PCT Published Application WO 89/10977.

Ordinarily the microfabricated apparatus is used in conjunction with a known detection technology particularly adapted to discriminating between bounded regions in which binding has taken place and those in which no binding has occurred and for quantitating the relative extent of binding in different bounded regions. In DNA and RNA sequence detection, autoradiography and optical detection are advantageously used. Autoradiography is performed using $^{32}$P or $^{35}$S labelled samples. For traditional DNA sequence analysis applications, nucleic acid fragments are end-labeled with $^{32}$P and these end-labeled fragments are separated by size and then placed adjacent to x-ray film as needed to expose the film, a function of the amount of radioactivity adjacent to a region of film. Alternatively, phophorimager detection methods may be used.

Optical detection of fluorescent-labelled receptors is also employed in detection. In traditional sequencing, a DNA base-specific fluorescent dye is attached covalently to the oligonucleotide primers or to the chain-terminating dideoxynucleolides used in conjunction with DNA polymerase. The appropriate absorption wavelength for each dye is chosen and used to excite the dye. If the absorption spectra of the dyes are close to each other, a specific wavelength can be chosen to excite the entire set of dyes. One particularly useful optical detection technique involves the use of ethidium bromide, which stains duplex nucleic acids. The fluorescence of these dyes exhibits an approximate twentyfold increase when it is bound to duplexed DNA or RNA, when compared to the fluorescence exhibited by unbound dye or dye bound to single-stranded DNA. This dye is advantageously used to detect the presence of hybridized polynucleic acids.

A highly preferred method of detection is a charge-coupled-device array or CCD array. With the CCD array, a individual pixel or group of pixels within the CCD array is placed adjacent to each confined region of the substrate where detection is to be undertaken. Light attenuation, caused by the greater absorption of an illuminating light in test sites with hybridized molecules, is used to determine the sites where hybridization has taken place. Lens-based CCD cameras can also be used.

Alternatively, a detection apparatus can be constructed such that sensing of changes in AC conductance or the dissipation of a capacitor placed contiguous to each confined region can be measured. Similarly, by forming a transmission line between two electrodes contiguous to each confined region hybridized molecules can be measured by the radio-frequency (RF) loss. The preferred methods for use herein are described in, *Optical and Electrical Methods and Apparatus for Molecule Detection*. PCT Published Application WO 93/22678, published Nov. 11, 1993, and expressly incorporated herein by reference.

Methods for attaching samples of substantially homogeneous biomolecules of a pre-determined structure to the confined regions of the microapparatus are likewise known. One preferred method of doing so is to attach these biomolecules covalently to surfaces such as glass or gold films. For example, methods for attachments of oligonucleotide probes to glass surfaces are known. A primary amine is introduced at one terminus during the chemical synthesis thereof. Optionally, one or more triethylene glycol units may be introduced therebetween as spacer units. After derivatizing the glass surface in the confined region with epoxysilane, the primary amine terminus of the oligonucleotide can be covalently attached thereto.

See Beattie, et al., cited above, for a further description of this technology for fixing the predetermined biomolecules in the bounded regions of the microfabricated apparatus.

Related Art

Khrapko, K. R., et al., *A method for DNA sequencing by hybridization with oligonucleotide matrix*, J. DNA Sequencing and Mapping, 1:375–388 (1991), Drmanac, Radoje, et al., *Sequencing by hybridization: Towards an automated sequencing of one million M13 clones arrayed on membranes* Electrophoresis 13:566–573 (1992), Meier-Ewert, Sebastian, *An automated approach to generating expressed sequence catalogues*, Nature 361:375–376 (1993), Drmanac, R., et al., *DNA Sequence Determination by Hybridization: A Strategy for Efficient Large-Scale Sequencing*, Science 260:1649–1652 (1993), Southern, E.

M., et al., *Analyzing and Comparing Nucleic Acid Sequences by Hybridization to Arrays of Oligonucleotides: Evaluation Using Experimental Models*, Genomics 13:1008–1017 (1992), and Saiki, Randall K., et al., *Genetic analysis of amplified DNA with immobilized sequence-specific oligonucleotide probes*, Proc. Natl. Acad. Sci. USA 86:6230–6234 (1989) describe sequence-by-hybridization determinations, including via the use of arrays of oligonucleotides attached to a matrix or substrate. Eggers, Mitchell D., et al., *Genosensors: microfabricated devices for automated DNA sequence analysis*, SPIE Proceedings Series, Advances in DNA Sequence Technology, Proceedings Preprint, The International Society for Optical Engineering, 21 Jan. 1993; Beattie, Kenneth, et al., *Genosensor Technology*, Clinical Chemistry 39:719–722 (1993); Lamture, J. B., et al., *Direct detection of nucleic acid hybridization on the surface of a charge coupled device*, Nucl. Acids Res. 22:2121–2124 (1994); and Eggers, M., et al., *A microchip for quantitative detection of molecules utilizing luminescent and radioisotope reporter groups*, Biotechniques 17:516–525 (1994) describe the general strategies and methodologies for designing microfabricated devices useful in sequencing by hybridization (SBH) for DNA.

SUMMARY OF THE INVENTION

The present invention particularly provides:

(a) In a microfabricated device comprising (1) a substrate containing a multiplicity of discrete and isolated regions arrayed across a surface thereof and adapted to interact with or integrally interacting with a detecting means capable of identifying and addressing each of said regions and determining and reporting whether a binding reaction has taken place therein, and (2) essentially homogeneous samples of biomolecules of pre-determined structures fixed in each of said discrete and isolated regions, such that the detection of a binding reaction between said biomoleculep in one or more of said regions and a test sample provides information capable of identifying or otherwise characterizing the molecular species in said test sample, the improvement that comprises:

discrete and isolated regions that extend through said substrate and terminate on a second surface thereof such that said test sample upon contact with said substrate is capable of penetrating therethrough during the course of said binding reaction.

(b) The improvement above wherein said biomolecules are oligonucleotides and said test sample comprises polynucleic acids.

(c) The improvement above wherein said substrate is a nanoporous glass wafer.

(d) The improvement above wherein said discrete and isolated regions comprise tapered conical wells bonded to one face of said nanoporous glass wafer.

(e) The improvement above comprising a high density array, wherein each of said discrete and isolated regions on said nanoporous glass wafer has a largest diameter of about 100 $\mu$m, the spacing between adjacent regions is about 500 $\mu$m, said wafer is about 100 $\mu$m in thickness, whereby the volume of said region within the wafer is about 40 nL and the density of said regions on said wafer is about 400 regions/cm$^2$.

(f) The improvement above comprising an ultra-high density array, wherein each of said discrete and isolated regions on said nanoporous glass wafer has a largest diameter of about 50 $\mu$m, the spacing between adjacent regions is about 150 $\mu$m, said wafer is about 50 $\mu$m in thickness, whereby the volume of said region within the wafer is about one nL and the density of said regions on said wafer is about 4,400 regions/cm$^2$.

(g) The improvement above comprising an array, wherein each of said discrete and isolated regions on said nanoporous glass wafer has a largest diameter of from about 5 $\mu$m to about 2000 $\mu$m, the spacing between adjacent regions is from about 0.1 to 10 times said largest diameter, and said wafer is from about 10 $\mu$m to about 500 $\mu$m in thickness.

(h) The improvement above wherein the contact between said test sample and said discrete and isolated regions is by flooding the first surface of said substrate with said test sample and placing said second surface of said substrate under negative pressure relative to said first surface, whereby the resulting vacuum facilitates the flow through said substrate.

(i) The improvement above wherein said oligonucleotides are fixed in said isolated and discrete regions on said substrate by attaching a terminal primary amine derivative of said oligonucleotide to a glass substrate derivatized with epoxysilane.

(j) The improvement above wherein said oligonucleotide-silane fixation comprises the incorporation of one or more triethylene glycol phosphoryl units, whereby optimal spacing between said glass surface and the base pairs of said oligonucleotide is achieved.

(k) The improvement above wherein said oligonucleotides are fixed in said isolated and discrete regions on said substrate by attaching a terminal bromoacetylated amine derivative of said oligonucleotide to a platinum or gold substrate derivatized with a dithioalkane.

(l) The improvement above wherein said detection of said binding reaction is detection by a charge-coupled device (CCD) employed to detect hybridization of radioisotope-, fluorescent-, or chemiluminescent-labelled polynucleic acids.

(m) A microfabricated device for simultaneously conducting a multiplicity of binding reactions, comprising:

(1) a substrate providing a rigid support for said device;

(2) an array of discrete and isolated regions arranged across a surface of said substrate and extending therethrough to a second surface of said substrate, thereby forming pores in said substrate;

(3) substantially homogeneous samples of a predetermined set of biomolecules, each such sample being fixed in one or more of said regions, such that one or more of said biomolecules is capable of binding with a molecular species in a test sample passing therethrough; and (4) a detection means capable of determining for each such region whether a binding reaction has taken place and reporting the result thereof.

(n) A device as described above further comprising a means for providing fluidic flow through the substrate.

(o) In a method for using a microfabricated device for the identification of the molecular species contained in a test sample, said device comprising (1) a substrate containing a multiplicity of discrete and isolated regions arrayed across a surface thereof and adapted to interact with or integrally interacting with a detecting means capable of characterizing or otherwise identifying and addressing each of said regions and determining and reporting whether a binding reaction has taken place therein, and (2) essentially homogeneous samples of biomolecules of pre-determined structures fixed in each of said discrete and isolated regions, such that the detection of a binding reaction between said biomolecules in one or more of said regions and said test sample provides information capable of characterizing or otherwise identifying the molecular species in said test sample, the improvement that comprises:

allowing said test sample, during the course of said binding reaction, to penetrate through said discrete and isolated regions by constructing said regions to contain pores that extend through said substrate and terminate on a second surface thereof.

The devices of the present invention are used to characterize or otherwise identify molecular species capable of controllably binding to biomolecules in the same manner and using the same binding regimens as are known in the art. Although uses of these novel devices include antibody-antigen and ligand-receptor binding, a major use of the present invention is in the field of nucleic acid sequence analysis. Two fundamental properties of DNA are vital to its coding and replicational functions in the cell:

(1) The arrangement of "bases" [adenenine (A), guanine (G), cytosine (C) and thymine (T)] in a specific sequence along the DNA chain defines the genetic makeup of an individual. DNA sequence differences account for the differences in physical characteristics between species and between different individuals of a given species (2) One strand of DNA can specifically pair with another DNA strand to form a double-stranded structure in which the bases are paired by specific hydrogen bonding: A airs with T and G pairs with C. Specific pairing also occurs between DNA and another nucleic acid, ribonucleic acid (RNA), wherein uracil (U) in RNA exhibits the same base airing properties as T in DNA.

The specific pattern of base pairing (A with T or U and G with C) is vital to the proper functioning of nucleic acids in cells, and also comprises a highly specific means for the analysis of nucleic acid sequences outside the cell. A nucleic acid strand of specific base sequence can be used as a sequence recognition element to "probe" for the presence of the perfectly "complementary" sequence within a nucleic acid sample (Conner, et al., *Proc. Natl. Acad. Sci., U.S.A.*, 80:278–282 (1983)). Thus, if a sample of DNA or RNA is "annealed" or "hybridized" with a nucleic acid "probe" containing a specific base sequence, the probe will bind to the nucleic acid "target" strand only if there is perfect (or near-perfect) sequence complementarity between probe and target. The hybridization event which indicates the presence of a specific base sequence in a nucleic acid sample is typically detected by immobilization of the nucleic acid sample or the probe on a surface, followed by capture of a "tag" (for example, radioactivity or fluorescence) carried by the complementary sequence.

DNA hybridization has been employed to probe for sequence identity or difference between DNA samples, for example in the detection of mutations within specific genetic regions (Kidd, et al., N. Engl. J. Med., 310:639–642 (1984); Saiki, et al., N. Engl. J. Med., 319:537–541 (1988); Saiki, et al., Proc. Natl. Acad. Sci., U.S.A., 86:6230–6234 (1989)). Although DNA probe analysis is a useful means for detection of mutations associated with genetic diseases, the current methods are limited by the necessity of performing a separate hybridization reaction for detection of each mutation. Many human genetic diseases, for example, cancer (Hollstein, et al., Science, 253:49–53 (1991)) are associated with any of a large number of mutations distributed at many locations within the affected genes. In these cases it has been necessary to employ laborious DNA sequencing procedures to identify disease-associated mutations. The problem is compounded when there is a need to analyze a large number of DNA samples, involving populations of individuals. Detection of mutations induced by exposure to genotoxic chemicals or radiation is of interest in toxicology testing and population screening, but again, laborious, costly and time consuming procedures are currently necessary for such mutational analyses.

In addition to causing genetic diseases, mutations are also responsible for DNA sequence polymorphisms between individual members of a population. Genetic polymorphisms are DNA sequence changes at any given genetic locus which are maintained in a significant fraction of the individuals within a population. DNA sequence polymorphisms can serve as useful markers in genetic mapping when the detectable DNA sequence changes are closely linked to phenotypic markers and occur at a frequency of at least 5% of the individuals within a population. In addition, polymorphisms are employed in forensic identification and paternity testing. Currently employed methods for detecting genetic polymorphisms involve laborious searches for "restriction fragment length polymorphisms" (RFLPS) (Lander and Bottstein, Proc, Natl. Acad, Sci., U.S.A., 83:7353–7357 (1986)), the likewise laborious use of gel electrophoretic DNA length analysis, combined with a DNA amplification procedure which utilizes oligonucleotide primers of arbitrary sequence (Williams, et al., Nucl. Acids Res., 18:65316535 (1991); Welsh and McClelland, Nucl. Acids Res., 18:7213-7218 (1991)), and the gel electrophoretic analysis of short tandem repeat sequences of variable length) in genomic DNA. Weber, James L., Genomics 7: 524–530 (1990) and Weber, James L., Am. J. Hum. Genet. 44: 388–396 (1989).

Another kind of DNA sequence variation is that which occurs between species of organisms, which is of significance for several reasons. First, identification of sequence differences between species can assist in the determination of the molecular basis of phenotypic differences between species. Second, a survey of sequence variation within a specific gene among numerous related species can elucidate a spectrum of allowable amino acid substitutions within the protein product encoded by the gene, and this information is valuable in the determination of structure-function relationships and in protein engineering programs. However, this type of targeted DNA sequence comparison is extremely laborious, time consuming and costly if carried out by current DNA sequencing methodology. Additionally, genetic sequence variation can form the basis of specific identification of organisms, for example, infectious microorganisms.

The apparatus of the present invention is employed in a variety of analytical tasks, including nucleic acid sequence analysis by hybridization, analysis of patterns of gene expression by hybridization of cellular MRNA to an array of gene-specific probes, immunochemical analysis of protein mixtures, epitope mapping, assay of receptor-ligand interactions, and profiling of cellular populations involving binding of cell surface molecules to specific ligands or receptors immobilized within individual binding sites. Although nucleic acid analysis is specifically taught in this disclosure, the present invention can be equally applied to a broad range of molecular binding reactions involving small molecules, macromolecules, particles, and cellular systems.

DETAILED DESCRIPTION

Figure 1:
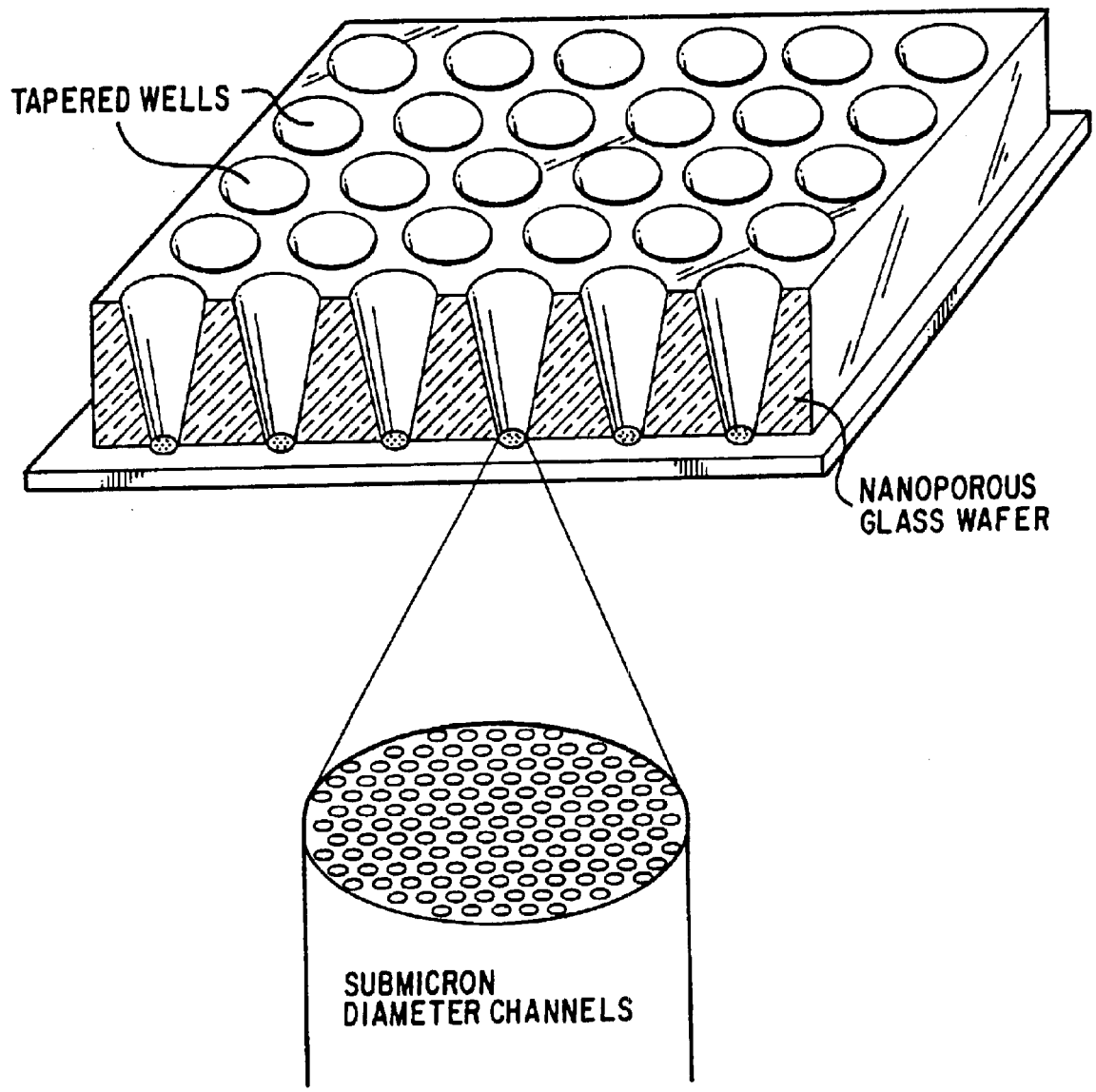
FIG. 1 depicts the use of an array of tapered sample wells that comprise a rigidifying support member for the porous wafer containing 0.1–10 micron diameter channels comprising the bonding region for the biomolecules fixed therein. As described below, the binding region is a microporous or nanoporous glass wafer to which the upper polymeric layer is attached.
Figure 2:
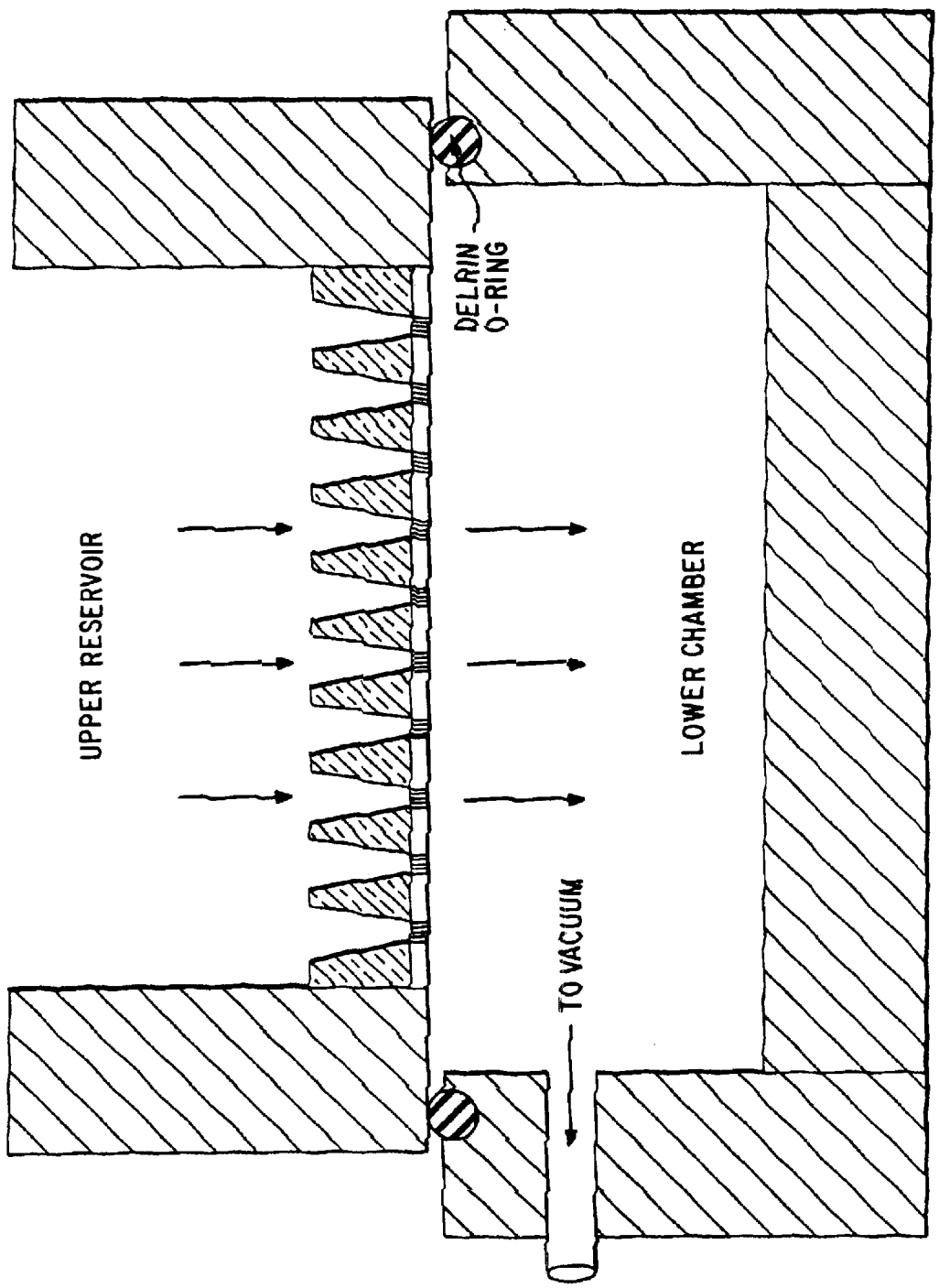
FIG. 2 depicts the packaging of a wafer substrate in a sealed lower chamber to which a vacuum may be applied such that material applied to an upper reservoir contacts with the upper surface of the porous substrate is driven through the sample wells. Specifically depicted in FIG. 2 is the use of a Delrin O-Ring comprising the wafer-lower chamber seal.

The present invention is more readily understood through the following preferred embodiments:

EXAMPLE 1

Nanochannel Glass (NCG) Wafers

Two types of nanochannel glass arrays developed at the Naval Research Laboratory are used as high surface area nanoporous support structures to tether DNA targets or probes for hybridization. NCG materials are unique glass structures containing a regular geometric array of parallel holes or channels as small as 33 nm in diameter or as large as several micrometers in diameter. See Tonucci, R. J., Justus, B. L., Campillo, A. J. and Ford, C. E. 1992. Science 258:783–785. These nanochannel glass structures can possess packing densities in excess of $3 \times 10^{10}$ channels per square centimeter, fabricated in various array configurations. A variety of materials can be immobolized or fixed to the glass surfaces within the channels of the NCG array, to yield a high surface area to volume ratio.

Nanochannel glass arrays are fabricated by arranging dissimilar glasses in a predetermined configuration, where at least one glass type is usually acid etchable. Construction of a two-dimensional hexagonal close packing array begins by insertion of a cylindrical acid etchable glass rod (referred to as the channel glass) into an inert glass tube (referred to as the matrix glass) whose inner dimensions match that of the rod. The pair is then drawn under vacuum to reduce the overall cross-section to that of a fine filament. The filaments are then stacked, re-fused and redrawn. This process is continued until appropriate channel diameters and the desired number of array elements are achieved. By adjusting the ratio of the diameter of the etchable glass rod to that of the outside dimension of the inert glass tubing, the center-to-center spacing of the rods and their diameters in the finished product become independently adjustable parameters. Once the fabrication process is complete, the NCG material is wafered perpendicular to the direction of the channels with a diamond saw and then polished to produce 0.1–1.0 mm sections of material. The channel glass of the array structure is then etched away with an acid solution.

A hexagonal close packing arrangement of channel glasses, after acid etching, contains typically $10^7$ channels and is uniform throughout. The channel diameter is typically 450 nm and the center-to-center spacing is approximately 750 nm. The type of array structure described above is useful in the NCG array hybridization assembly in accordance with the present invention. In this configuration, the tapered sample well structure defines each group of channels serving as a specific hybridization test site.

A second type of hexagonal array structure, in which separated clusters of channels are formed during the fabrication process, exhibits an open array structure with typical channel diameters of 300nm. The overall glass structure consists of an array of 18 µm diameter subarrays, each serving to contain a specific DNA probe or target, and spaced typically 25 µm apart from neighboring arrays.

EXAMPLE 2

Well Arrays Defining Discrete and Isolated Binding Regions

The NCG hybridization arrays described in Example 1 are bonded on the upper side to a polymeric layer containing an array of orifices which align with the array of nanochannel bundles and serve as sample wells for placement of a substantially homogeneous sample of a biomolecule (e.g., a single DNA species) within each hybridization site. This polymeric sample well array also provides physical support to the fragile NCG wafer.

The polymeric array of orifices are fabricated using methods known in the art. For example, this polymeric layer suitable for use herein can be obtained from MicroFab Technologies, Inc. The orifices are fabricated using excimer laser machining. This method is preferred because existing technology is employed allowing for low cost/high volume manufacturing, as is currently being done in the microelectronics industry.

Development of the polymeric array comprises four task: (1) materials selection; (2) ablation tooling and process development; (3) lamination tooling and process development; and (4) production of high density and ultra-high density polymeric arrays. These tasks are undertaken as follows:

Part A: Materials selection.

The materials useful in the polymeric array are filled polymers, epoxy resins and related composite (e.g., "circuit-board"-type) materials. Because it is a standard process in the microelectronics industry, the present invention most advantageously employs polymeric materials with the adhesive applied by the commercial vendor of the material. for example, a polyamide with a 12 µm thick layer of a B-stage (heat curing) adhesive The primary requirements for the polymeric array material to be used are:

1. High suitability for excimer laser machinability:
   i. high absorption in UV (e.g., >4×10$^5$/cm at 193 nm),
   ii. high laser etch rate (e.g., 0.5 μm/pulse) and low hole taper (reduction in hole diameter with depth into material, e.g., <3°);
2. Obtainable in thicknesses up to 1 mm;
3. Obtainable with B-stage adhesive on one side which is both laser ablatable and suitable for bonding to the nanoporous wafer;
4. High rigidity and thermal stability (to maintain accurate alignment of samplewell and NCG wafer features during lamination);
5. Compatibility with DNA solutions (i.e., low nonspecific binding)

Part B: Ablation Tooling and Processing

Contact mask excimer laser machining is a preferred processing technique because it is a lower cost technique than projection mask excimer laser machining. A projection mask is, however, employed when the feature size less than 50 μm. One or more masks with a variety of pattern sizes and shapes are fabricated, along with fixtures to hold the mask and material to be ablated. These masks are employed to determine the optimal material for laser machining and the optimal machining conditions (i.e., mask hole size, energy density, input rate, etc.). Scanning electron microscopy and optical microscopy are used to inspect the excimer laser machined parts, and to quantify the dimensions obtained, including the variation in the dimensions.

In addition to ablating the sample wells into the polymeric material, the adhesive material is also ablated. This second ablation is undertaken so that the diameter of the hole in the adhesive is made larger than diameter of the sample well on the adhesive side of the polymeric material. This prevents the adhesive from spreading into the sample well and/or the nanoporous glass during lamination.

Part C: Lamination Tooling and Processing

Initial lamination process development is carried out using unablated polymeric material (or alternatively, using glass slides and/or silicon wafers). Cure temperature, pressure, and fixturing are optimized during this process development. Thereafter, the optimized processing parameters are employed to laminate both nanoporous wafers and polymeric arrays. The final lamination is done such that the alignment of the two layers creates functional wells.

Part D: Production of Polymeric Arrays

The optimal mask patterns and excimer laser parameters are determined and thereafter employed in the manufacture of contact masks and material holding fixtures. Typically, fabrication is done so as to produce a large number (>100) of parts as the masks wear out with use).

EXAMPLE 3

Porous Silicon Wafers

Two general types of porous silicon devices are prepared according to the process described herein. First, known microfabrication methods are used to fabricate wafers, bounded by integral sample wells. Second, uniformity porous wafer structures are bonded to the same orifice sample well arrays that were described previously (Example 2) for NCG glass arrays. Porous silicon designs are advantageously employed herein because of their adaptability to low cost mass production processes and their ability to incorporate in the fabrication process structural elements that function in fluidic entry and exit from the hybridization site and structures (e.g., electrodes) that may function in hybridization detection. Stable, open-cell porous materials are used to accomplish enhancements and to introduce qualitatively new features in these devices, whereby the surface area of discrete and isolated binding regions is increased by a factor of 100 to 1000 in hybridization-based electronic, fluorescence and radiation-based DNA detectors. In accomplishing this objective, controlled introduction of high-surface-area supports at the surface detection site is employed.

Thin-film processing technology is used to deposit chemically inert and thermally stable microporous materials. Materials and processing methods are selected to achieve low-cost semiconductor batch fabrication of integrated semiconductor detectors. The microchip device provides in situ multisite analysis of binding strength as ambient conditions are varied. Porous silicon materials are fabricated in oriented, pore arrays or random interconnected networks and with pore diameters selected over the range from 2 nm to several micrometers.

Porous silicon is produced most easily through electrochemical etching. It can be processed into two important pore structures, interconnected networks and oriented arrays. The pore diameter is tailored from approximately 2 nm to micrometer dimensions by selection of doping and electrochemical conditions. For n-type material, etching is thought to proceed through a tunneling mechanism in which electrons are injected into the pore surface through field concentration effects. In the case of p-type material the mechanism seems to be through moderation of carrier supply at the electrolyte/silicon interface. In practice, the following structures can be fabricated:

i) a dense interconnected network layer with porosity of 40–60% and silicon filament size in the nanometer size regime. This is most easily obtained in lightly doped (<1 Ω-cm resistivity) p-type silicon.

ii) a interconnected branched network of pores of typically 10-nm diameter, axis preferentially oriented along <100> direction, and porosity of 30–80% depending on etching conditions. This is obtained in p-type material of $10^{-1}$ to $10^{-2}$ Ω-cm resistivity.

iii) dense oriented arrays of pores oriented with axis along <100>direction and with pore diameters in the range of 10 to 100 nm. Obtained in p-type material with resistivity less than $10^{-2}$ ω-cm.

iv) dense oriented arrays of pores oriented along <100> direction and with pore diameters in the range less than 10 nm. Obtained in n-type material with resistivity between $10^{-1}$ and $10^{-2}$ Ω-cm.

v) dense oriented arrays of rectangular pores oriented with axis along <100> direction, rectangle side defined by {001} planes, and with pore diameters in the range less than 100 nm. Obtained in p-type material with resistivity between $10^{-1}$ and $10^{-2}$ Ω-cm.

vi) low density interconnected networks of large (1-μm-diameter) pores. This occurs in lightly doped n-type material.

These materials are fabricated on the device structures described above.

Characterization can be undertaken by scanning electron microscopy. The surface wetting properties are varied using vapor treatment with silylation materials and chlorocarbons.

High-porosity dielectrics which function as molecular sieves are produced by nuclear track etching. While nuclear track etching is used to produce these molecular sieves in a wide range of inorganic materials, it is most often used with dielectrics such as mica and sapphire. In this method, described in U.S. Pat. No. 3,303,085 (Price, et al.), a substrate is first bombarded with nuclear particles (typically several MeV alpha particles) to produce disturbances or "tracks" within the normal lattice structure of the material and then wet-etched to produce pores which follow the tracks caused by the nuclear particles. More specifically, Price et al. disclose that the exposure of a mica substrate to heavy, energetic charged particles will result in the formation of a plurality of substantially straight tracks in its lattice structure and that these tracks can be converted into pores by wet etching the substrate.

Pore sizes and overall porosity are variably controllable with pores typically 0.2 μm in diameter and densities on the order of $10^9/cm^2$. Particle track depths are energy dependent on the incident particle beam, but resulting pores can be extended through an entire 500-μm-thick substrate. Incorporation of these materials on the device structures shown above is readily accomplished. In addition, the use of implantation-etched dielectrics as the sensor element has advantages versus the porous silicon approach since the material is hydrophilic.

Figure 3:
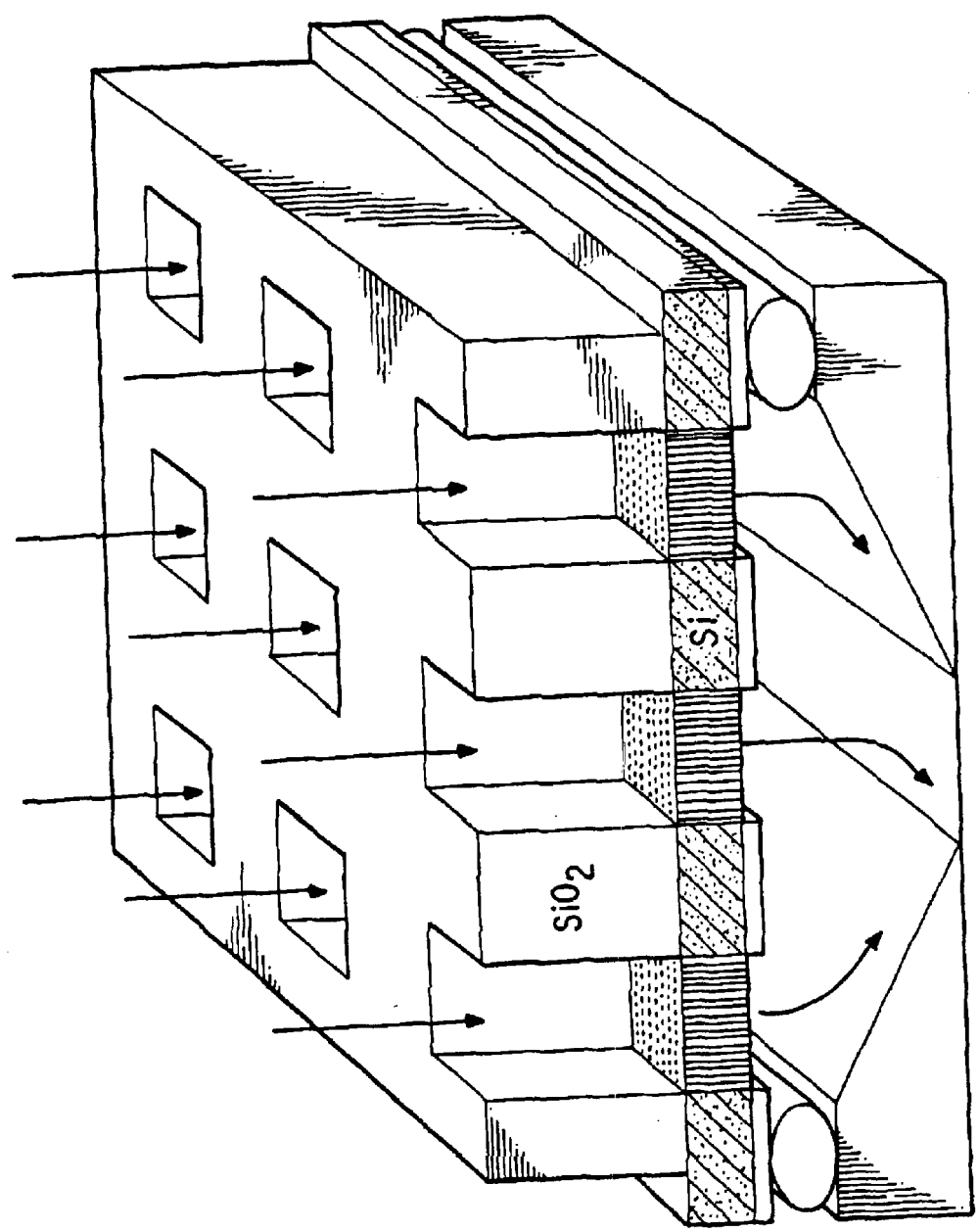
FIG. 3 depicts a porous silicon wafer with integral sample wells. Procedures for constructing the depicted device are described in Example 3.

A preferred device is the porous silicon array wafer with integral sample wells illustrated in FIG. 3. This may be constructed as follows: A four inch diameter, 100 μm thick wafer of crystalline silicon (n-type, doped with $10^{15}$ P/$cm^3$) with axis oriented along <100> direction is coated with photoresist and exposed to light through a mask to define a 50×50 array of 200 μm square areas having 200 μm space between them across the 2 cm×2cm central area of the wafer. The process described by V. Lehmann (*J. Electrochem. Soc.* 140(100):2836–2843 (1993)) is then used to create patches of closely spaced pores of diameter 2–5 μm, oriented perpendicular to the wafer surface, within each square area defined in the photolithographic step. A 300 μm thick wafer of silicon dioxide is coated with photoresist and exposed to light through the same mask used to define 200 μm square porous regions in the silicon wafer, and acid etching is conducted to create 200 μm square holes in the silicon dioxide wafer. The silicon dioxide wafer is then aligned with and laminated to the porous silicon wafer using a standard wafer bonding process to form the integral structure shown in the figure. During the high temperature annealing step, the silicon surface of each pore is oxidized to form a layer of silicon dioxide. The epoxysilane-amine linkage procedure described in EXAMPLE 4 is then carried out to covalently attach amine-containing biopolyrner species to the walls of the pores.

EXAMPLE 4

Oligonucleotide Attachment to GlassISiO$_2$

Part A: Epoxysilane Treatment of Glass

A stock solution of epoxysilane is freshly prepared with the following proportions: 4 ml 3-glycidoxypropyl-trimethoxysilane, 12 ml xylene, 0.5 ml N,N-diisopropylethylamine (Hunig's base). This solution is flowed into the pores of the wafer, then the wafer is soaked for 5 hours in the solution at 80° C., then flushed with tetrahydrofuran, dried at 80° C., and placed in a vacuum desiccator over Drierrite or stored in a desiccator under dry argon.

Part B: Attachment of Oligonucleotide

Oligonucleotide, bearing 5'- or 3'-alkylamine (introduced during the chemical synthesis) is dissolved at 10 μM–50 μM in water and flowed into the porous silica wafer. After reaction at 65° C. overnight the surface is briefly flushed with water at 65° C., then with 10 mM triethylamine to cap off the unreacted epoxy groups on the surface, then flushed again with water at 65° C. and air dried. As an alternative to attachment in water, aminederivatized oligonucleotides can be attached to epoxysilane-derivatized glass in dilute (eg., 10 mM–50 mM) KOH at 37° C. for several hours, although a higher background of nonspecific binding of target sample DNA to the surface (independent of base pairing) may occur during hybridization reaction.

EXAMPLE 5

Robotic Fluid Delivery

A Hamilton Microlab 2200 robotic fluid delivery system, equipped with special low volume syringes and 8-position fluid heads, capable of delivering volumes of 10–100 nl at 500 μm xyz stepping and a few percent precision. Using this equipment 40-nl samples of biomolecules (e.g., DNA, olgionucleotides and the like) are placed into the wells of the high density NCG wafer. A piezoelectrically controlled substage custom fitted for the Microlab 2200 permits xy positioning down to submicron resolution. For 1-nl samples, custom fabricated needles are employed. The eight-needle linear fluid head is operated in staggered repetitive steps to generate the desired close spacing across the wafer. The system has a large stage area and rapid motion control, providing the capacity to produce hundreds of replicate hybridization wafers.

Part A: Microfab Microfluidic Jets

Methods are known in the art (Microfab Technologies, Inc.) for delivering subnanoliter microdroplets of fluids to a surface at submicron precision. A microjet system capable of delivering subnanoliter DNA solutions to the wafer surface is employed as follows: For placement of DNA into individual hybridization sites within ultra-high density wafers, with volumes of one nl (corresponding to a 130μm sphere or 100 μm cube) commercially available dispensing equipment using inkjet technology as the microdispensing method for fluid volume below is employed. The droplets produced using ink-jet technology are highly reproducible and can be controlled so that a droplet may be placed on a specific location at a specific time according to digitally stored image data. Typical droplet diameters for demand mode ink-jet devices are 30–100 μm, which translates to droplet volumes of 14–520 pl. Droplet creation rates for demand mode ink-jet devices are typically 2000–5000 droplets per second. Thus, both the resolution and throughput of demand mode ink-jet microdispensing are in the ranges required for the ultrahigh density hybridization wafer.

Part B: Microdispensing System

The microdispensing system is modified from a MicroFab drop-on-demand ink-jet type device, hereafter called a MicroJet device such that this type of device can produce 50cm diameter droplets at a rate of 2000 per second. The operating principles of this type of device are known (D. B. Wallace, "A Method of Characteristics Model of a Drop-On-Demand Ink-Jet Device Using an Integral Drop Formation Method," ASME publication 89-WA/FE4, December 1989) and used to effect the modification. To increase throughput, eight of these devices are integrated into a line array less than 1 inch (25mm) long. The eight devices are loaded with reagent simultaneously, dispense sequentially, and flush simultaneously. This protocol is repeated until all of the reagents are dispensed. Most of the cycle time is associated with loading and flushing reagents, limiting the advantages of a complex of parallel dispensing capability. Typical cycle time required is as on the following order: I minute for flush and load of 8 reagents; 30 seconds to calibrate the landing location of each reagent; 15 seconds to dispense each reagent on one location of each of the 16 genosensors, or 2 minutes to dispense all 8 reagents. Total time to load and dispense 8 reagents onto 16 sensors is thus 3.5 minutes. Total time for 64 reagents onto 16 sensors would be 28 minutes. The microdispensing system will consist of the subsystems listed below:

A. MicroJet Dispense Head—An assembly of 8 MicroJet devices and the required drive electronics. The system cost and complexity are minimized by using a single channel of drive electronics to multiplex the 8 dispensing devices. Drive waveform requirements for each individual device are downloaded from the system controller. The drive electronics are constructed using conventional methods.

B. Fluid Delivery System—A Beckman Biomec is modified to act as the multiple reagent input system. Between it and the MicroJet dispense head are a system of solenoid valves, controlled by the system controller. They provide pressurized flushing fluid (deionized water or saline) and air to purge reagent from the system and vacuum to load reagent into the system.

C. X-YPositioning System—A commercially available precision X-Y positioning system, with controller, is used. Resolution of 0.2 $\mu$m and accuracy of 2 $\mu$m are readily obtainable. The positioning system is sized to accommodate 16 sensors, but Microjet dispense head size, purge station, and the calibration station represent the main factors in determining overall size requirements.

D. Vision System—A vision system is used to calibrate the "landing zone" of each MicroJet device relative to the positioning system. Calibration occurs after each reagent loading cycle. Also, the vision system locates each dispensing site on each sensor when the 16 sensor tray is first loaded via fiducial marks on the sensors. For economy, a software based system is used; although a hardware based vision system can be advantageously employed.

E. System Controller—A standard PC is used as the overall system controller. The vision system image capture and processing also reside on the system controller.

EXAMPLE 6

Liquid Flow-Through

Figure 4:
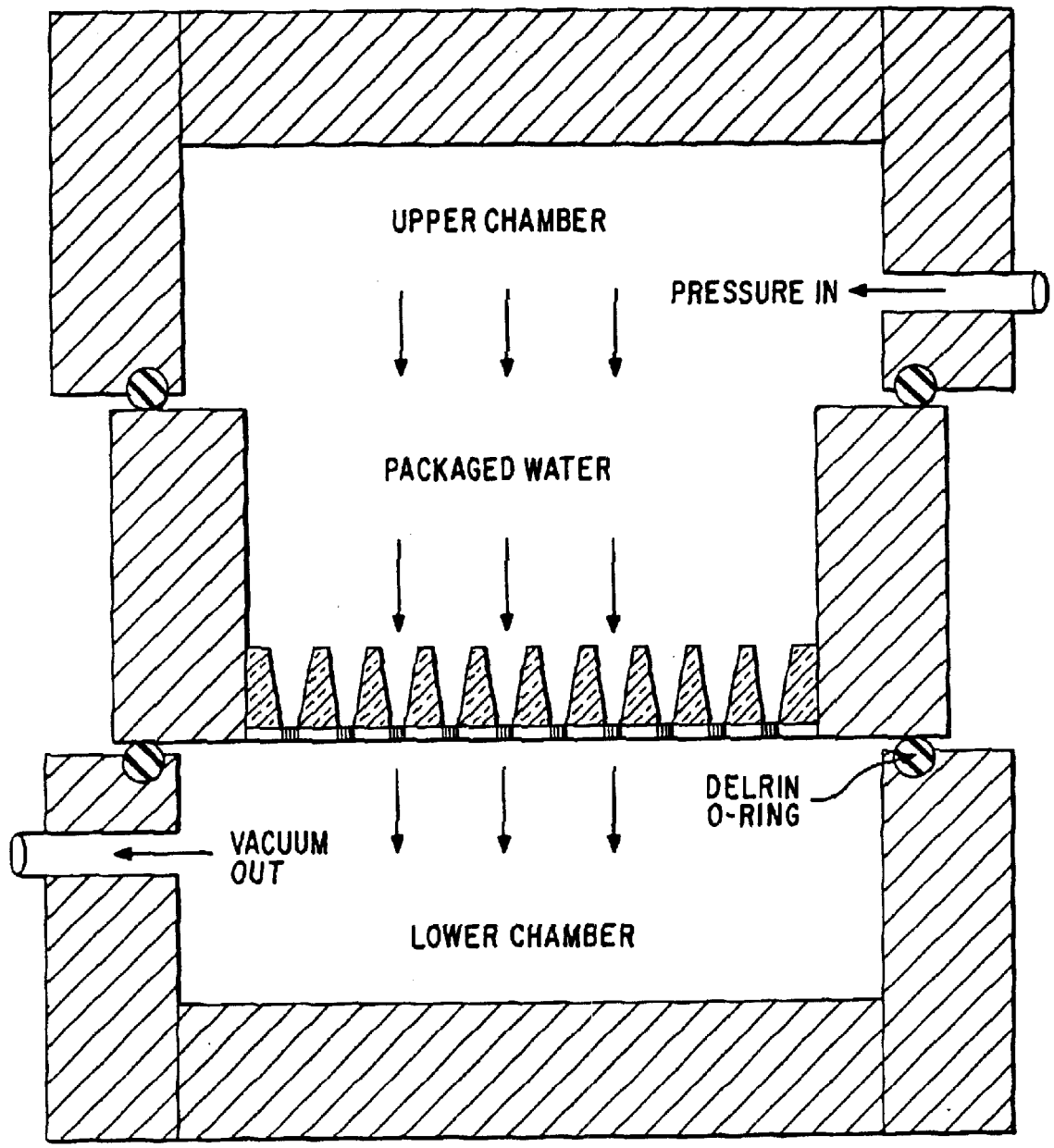
FIG. 4 depicts the same vacuum-containing wafer-lower chamber apparatus of FIG. 2 with an additionally optioral pressurized upper chamber. Again, as depicted, the upper chamber is sealed by use of a Delrin O-Ring.

In order to bind DNA probes or targets within the pores of the microfabricated hybridization support, carry out the hybridization and washing steps, process the material for re-use, and potentially recover bound materials for further analysis, a means is provided for flow of liquids through the wafer. To enable flow of liquid through the hybridization wafer, it is packaged within a 2 mm×4 mm polypropylene frame, which serves as an upper reservoir and structure for handling. A polypropylene vacuum chamber with a Delrin o-ring around its upper edge to permit clamping of the wafer onto the vacuum manifold to form a seal is employed. The vacuum assembly is illustrated in FIG. 4. For control of fluid flow through the wafer a screw-drive device with feedback control is provided.

EXAMPLE 7

Synthesis and Derivatization of Oligonucleotides

Oligonucleotides to be used in the present invention are synthesized by the phosphoramidite chemistry (Beaucage, S. L. and Caruthers, M. H. 1981. Tet. Lett. 22:1859–1862) using the segmented synthesis strategy that is capable of producing over a hundred oligonucleotides simultaneously (Beattie, K. L., Logsdon, N. J., Anderson, R. S., Espinosa-Lara, J. M., Maldonado-Rodriguez, R. and Frost, J. D. 111. 1988. Biotechnol. Appl. Biochem. 10:510–521; Beattie, K. L. and Fowler, R. F. 1991. Nature 352:548–54926,27). The oligonucleotides can be derivatized with the alkylamino function during the chemical synthesis, either at the 5'-end or the 3'-end.

Part A: Chemistry of Attachment to Glass

Optimal procedures for attachment of DNA to silicon dioxide surfaces are based on well-established silicon chemistry (Parkam, M. E. and Loudon, G. M. (1978) Biochem. Biophys. Res. Commun., 1:1–6; Lund, V., Schmid, R., Rickwood, D. and Hornes, E. (1988) Nucl. Acids Res. 16: 10861–10880). This chemistry is used to introduce a linker group onto the glass which bears a terminal epoxide moiety that specifically reacts with a terminal primary amine group on the oligonucleotides. This versatile approach (using epoxy silane) is inexpensive and provides a dense array of monolayers that can be readily coupled to terminally modified (amino- or thiol-derivatized) oligonucleotides. The density of probe attachment is controlled over a wide range by mixing long chain amino alcohols with the amine-derivatized oligonucleotides during attachment to epoxysilanized glass. This strategy essentially produces a monolayer of tethered DNA, interspersed with shorter chain alcohols, resulting in attachment of oligonucleotides down to 50 Å apart on the surface. Variable length spacers are optionally introduced onto the ends of the oligonucleotides, by incorporation of triethylene glycol phosphoryl units during the chemical synthesis. These variable linker arms are useful for determining how far from the surface oligonucleotide probes should be separated to be readily accessible for pairing with the target DNA strands. Thiol chemistry, adapted from the method of Whitesides and coworkers on the generation of monolayers on gold surfaces (Randall lee, T., Laibinis, P. E., Folkers, J. P. and Whitesides, G. M. (1991) Pure & Appl. Chem. 63: 821–828 and references cited therein.), is used for attachment of DNA to gold and platinum surfaces. Dithiols (e.g., 1, 10-decanedithiol) provide a terminal, reactive thiol moiety for reaction with bromoacetylated oligonucleotides. The density of attachment of DNA to gold or platinium surfaces is controlled at the surface-activation stage, by use of defined mixtures of mono- and dithiols.

Part B: Surface Immobilization of Recombinant Vector DNA , cDNA and PCR Fragments The chemical procedures described above are used most advantageously for covalent attachment of synthetic oligonucleotides to surfaces. For attachment of longer chain nucleic acid strands to epoxysilanized glass surfaces, the relatively slow reaction of surface epoxy groups with ring nitrogens and exocylic amino groups along the long DNA strands is employed to achieve immobilization. Through routine experimentation, optimal conditions for immobilization of unmodified nucleic acid molecules at a few sites per target are defined, such that the bulk of the immobilized sequence remains available for hybridization. In the case of immobilization tonanochannels coated with platinum or gold, hexylamine groups are first incorporated into the target DNA using polymerization (PCR or random priming) in the presence of 5-hexylarnine-dUTP, then a bromoacetylation step is carried out to activate the DNA for attachment to thiolated metal surfaces. Again, routine experimentation is employed (varying the dTTP/5-hexylamine-dUTP ratio and the attachment time) to define conditions that give reproducible hybridization results.

The foregoing procedure (omitting the bromoacetylation step) can also serve as an alternative method for immobilization of target DNA to glass surfaces.

Part C: DNA Binding Capacity

Based upon quantitative measurements of the attachment of labeled oligonucleotides to flat glass and gold surfaces, the end attachment places the probes 50–100 ÅA apart on the surface, corresponding to up to $10^8$ probes in a 50 $\mu$m×50 $\mu$m area. Approximately $10^{10}$–$10^{11}$ oligonucleotide probes can be tethered within a 50 $\mu$m cube of porous silicon in the nanofabricated wafer. The density of bound oligonucleotides per cross sectional area is estimated by end-labeling prior to the attachment reaction, then quantitating the radioactivity using the phosphorimager. Known quantities of labeled oligonucleotides dried onto the surface are used to calibrate the measurements of binding density. From data on the covalent binding of hexylamine-bearing plasmid DNA to epoxysilanized flat glass surfaces in mild base, it is known that at least $10^7$ pBR322 molecules can be attached per mmi of glass surface. Based on this density within the pores of the nanofabricated wafer, immobilization of $10^9$–$10^{10}$ molecules of denatured plasmid DNA per mm2 of wafer cross section are achieved.

EXAMPLE 8

Hybridization Conditions

Part A: Sample Preparation

The target DNA (analyte) is prepared by the polymerase chain reaction, incorporating [$^{32}$P]nucleotides into the product during the amplification or by using gamma-$^{32}$P[ATP]+ polynucleotide kinase to 5'-label the amplification product. Unincorporated label is removed by Centricon filtration. Preferably, one of the PCR fragments is 5'-biotin-labeled to enable preparation of single strands by streptavidin affinity chromatography. The target DNA is dissolved in hybridization buffer (50mM Tris-HCI, pH 8, 2 mM EDTA, 3.3M tetramethylammonium chloride) at a concentration of at least 5nM (5 fmol/$\mu$l) and specific activity of at least 5,000 cpm/fmol. PCR fragments of a few hundred bases in length are suitable for hybridization with surface-tethered oligonucleotides of at least octamer length.

Part B: Hybridization.

The target DNA sample is flowed into the porous regions of the chip and 5 incubated at 6° C. for 5–15 minutes, then washed by flowing hybridization solution through the porous chip at 18, C for a similar time. Alternatively, hybridization can be carried out in buffer containing 1M KCL or NaCl or 5.2M Betaine, in place of tetramethylammonium chloride.

Part C: Optimization of Hybridization Selectivity (Discrimination Against Mismatch-containing Hybrids Although the experimental conditions described above generally yield acceptable discrimination between perfect hybrids and mismatch-containing hybrids, some optimization of conditions may be desirable for certain analyses. For example, the temperature of hybridization and washing can be varied over the range 5° C. to 30° C. for hybridization with short oligonucleotides. Higher temperatures may be desired for hybridization using longer probes.

EXAMPLE 9

Quantitative Detection of Hybridization

Part A: Phosphorimager and Film Detection

The detection and quantitation of hybridization intensities is carried out using methods that are widely available: phosphorimager and film. The Biorad phosphorimager has a sample resolution of about 100 $\mu$m and is capable of registering both beta emission and light emission from chemiluminescent tags. Reagent kits for chemiluminescence detection available from Millipore and New England Nuclear, which produce light of 477 and 428 nm, respectively, are advantageously used with the Biorad instrument. Chemilurinescent tags are introduced into the target DNA samples (random-primed vector DNA or PCR fragments) using the procedures recommended by the supplier. Thereafter, the DNA is hybridized to the nanoporous wafers bearing oligonucleotide probes. Radioactive tags ($^{32}$P and $^{33}$P, incorporated by random priming and PCR reaction) are also used in these experiments. Film exposure is used for comparison. In the case of hybridization of labeled oligonucleotides with surface-immobilized target DNAS, most preferably the radioactive tags (incorporated using polynucleotide kinase) are used, since optimal chemiluminescent tagging procedures for oligonucleotides are generally not available.

Part B: CCD Detection Devices

CCD genosensor devices are capable of maximum resolution and sensitivity and are used with chemiluminescent, fluorescent and radioactive tags (Lamture, J. L., Varma, R., Fowler, R., Smith, S., Hogan, M., Beattie, K. L., Eggers, M., Ehrlick, D., Hollis. M. and Kosicki, B. 1993. Nature, submitted).

EXAMPLE 10

Genosensor Experiment; Mutation Detection in Exon 7/8 Region of Hamster hprn Gene The hprt gene is used extensively as a model system for studies of mutation. The gene has been cloned and sequenced from several manmnals. A variety of mutations in this gene are known and were characterized by DNA sequencing, in the hamster (induced by chemicals and radiation in Chinese Hamster Ovary cell lines) and from humans (associated with Lesch Nyhan syndrome). A significant fraction of hprt mutations are found in a short region of the gene encoded by exons 7 and 8. The nucleotide sequence of the normal and mutant genes are found in the following references: Edwards, A., Voss, H., Rice, P., Civitello, A., Stegemann, J., Schwager, C., Zinimermarn, J., Erfle, H., Caskey, C.T. and Ansorge, W. (1990), Automated DNA Sequencing of the Human HPRT Locus, Genomics, 6:593–608; Gibbs, R., Nguyen, P.-N., Edwards, A., Civitello, A. and Caskey, C. T. (1990), Multiplex DNA Deletion Detection and Exon Sequencing of the Hypoxanthine Phosphoribosyltransferase Gene in Lesch-Nyhan Families, Genomics, 7:235–244; Yu, Y., Xu, Z, Gibbs, R. and Hsie, A. (1992), Polymerase chain reaction-based Comprehensive Procedure for the Analysis of the Mutation Spectrum at the Hypoxanthine-guanine Phosphoribosyltransferase locus in Chinese Hamster Cells, Environ. Mol. Mutagen., 19:267–273; and Xu, Z., Yu, Y., Gibbs, R., Caskey, C. T. and Hsie, A. (1993), Multiplex DNA Amplification and Solid-phase Direct Sequencing at the hpn Locus in Chinese Hamster Cells, Mutat. Res., 282:237–248. The nucleotide sequence of the cDNA of hamster hprt exon 7/8 region is listed as follows:

```
                   500                  520                  540     (SEQ ID NO: 1)
GCAAGCTTGC TGGTGAAAAG GACCTCTCGA AGTGTTGGAT ATAGGCCAGA CTTTGTTGGA 560                  580                  600
TTTGAAATTC CAGACAAGTT TGTTGTTGGA TATGCCCTTG ACTATAATGA GTACTTCAGG

GATTTGAATC
```

The following represents the nucleotide sequence of hamster hprt genomic DNA in the exon 7/8 region where the CHO mutations are depicted above (1) and the human (h) and mouse (m) sequence differences below (1). The DNA sequence which begins with "5'-aacagCTTG" and which ends with "5'-GACTgtaag" is designated as SEQ ID NO:2 for sequences of hamster, human and mouse and SEQ ID NO:3 for the sequence of CHO cells. The remaining DNA, beginning with "5'-tacagTTGT" and ending with "GAATgtaat" is designated as SEQ ID NO:4 for sequences of hamster, human and mouse and SEQ ID NO:5 the sequence of CHO cells.

```
                              ----------
                                   ↑
-aacagCTTGCTGGTGAAAAGGACCTCTCGAAGTGTTGGATATAGGCCAG
                    ↓ ↓                  ↓ ↓
                    C A                  C A
                    h h                  m h
                              G          -
                              ↑          ↑
ACTgtaag----tacagTTGTTGGATTTGAAATTCCAGACAAGTTTGTTG
                +A                C
                ↑                 ↑
TTGGATATGCCCTTGACTATAATGAGTACTTCAGGGATTTGAATgtaat-
↓                    ↓          ↓
A                    A          A
h                    h          h
```

The small letters in the beginning of the sequence represent intron sequence on the 5'-side of exon 7. Some flanking intron sequence between exons 7 and 8 is shown (in small letters) on the second line, and at the end there is again a small stretch of intron sequence following exon 8. Underlined bases in the sequence represent mutations for which DNA samples are available, which can be used to demonstrate that a DNA chip targeted to this region can detect and identify mutations. Above the sequences are displayed mutations in hamster (CHO) cells induced by chemicals and radiation, including a 10-base deletion (top line), single base deletion (second line), single base insertion (third line) and single base substitutions (second and third lines). Below the sequences are shown single base differences between hamster and human (h) and mouse (m).

The set of oligonucleotide probes (of 8 mer- 10 mer in length) overlapping by two bases across the exon 7/8 region is depicted below for SEQ ID Nos:2–5:

```
            ----2----        ----4----        ----6----
    ----1----        ----3----        ----5----        --7--
-aacagCTTGCTGGTGAAAAGGACCTCTCGAAGTGTTGGATATAGGCCAG
                    ↓  ↓         ↓          ↓ ↓
                    C  A         -10        C A
            ----8-----        ----10----       -12-
-7-                  ----9-----       ----11---
ACTgtaag----tacagTTGTTGGATTTGAAATTCCAGACAAGTTTGTTG
                                 ↓        ↓
                                 G        -
  --12-       ----14---       ----16----       ----18---
      ----13---        ----15---       ----17---
```

```
                            -continued
TTGGATATGCCCTTGACTATAATGAGTACTTCAGGGATTTGAATgtaat
↓                    ↓   ↓                ↓
A                    +A  A                A
                                          C
```

This set of probes is selected to detect any of the mutations in this region, and the lengths are adjusted to compensate for base composition effects on in duplex stability (longer probes for AT-rich regions). The sequences of probes and primers are given in Table I, as follows:

TABLE I

OLIGONUCLEOTIDES FOR hprt MUTATION DETECTION

PCR primers for exons 7 & 8:

| Name | Sequence (5-3) | |
|---|---|---|
| MHEX71 | GTTCTATTGTCTTTCCCATATGTC | (SEQ ID NO:6) |
| MHEX82 | TCAGTCTGGTCAAATGACGAGGTGC | (SEQ ID NO:7) |
| HEX81 | CTGTGATTCTTTACAGTTGTTGGA | (SEQ ID NO:8) |
| HEX82 | CATTAATTACATTCAAATCCCTGAAG | (SEQ ID NO:9) |

9mer with amine at 5'-end:

| Name | Sequence (5'->3') | Name | Sequence (5'->3') |
|---|---|---|---|
| -A (554) | TGCTGGAAT | 1 | AGCAAGCTG |
| | | 2 | TTTCACCAG |
| +A (586/7) | ACTCATTTATA | 3 | AGGTCCTTT |
| | (SEQ ID NO:10) | 4 | CTTCGAGAG |
| -10 (509–518) | TATATGAGAG | 5 | TCCAACACT |
| | (SEQ ID NO:11) | 6 | GCCTATATC |
| A-G (545) | ATTCCAAATC | 7 | AGTCTGGC |
| | (SEQ ID NO:12) | 8 | TCCAACAACT |
| | | | (SEQ ID NO:13) |
| G-C (601) | CAAATGCCT | 9 | ATTTCAAATC |
| | | | (SEQ ID NO:14) |
| | | 10 | GTCTGGAAT |
| | | 11 | ACAAACTTGT |
| | | | (SEQ ID NO:15) |
| | | 12 | TCCAACAAC |
| | | 13 | GGGCATATC |
| | | 14 | TAGTCAAGG |
| | | 15 | ACTCATTATA |
| | | | (SEQ ID NO:16) |
| | | 16 | CTGAAGTAC |
| | | 17 | CAAATCCCT |
| | | 18 | AATTACATTCA |
| | | | (SEQ ID NO:17) |

Figure 5:
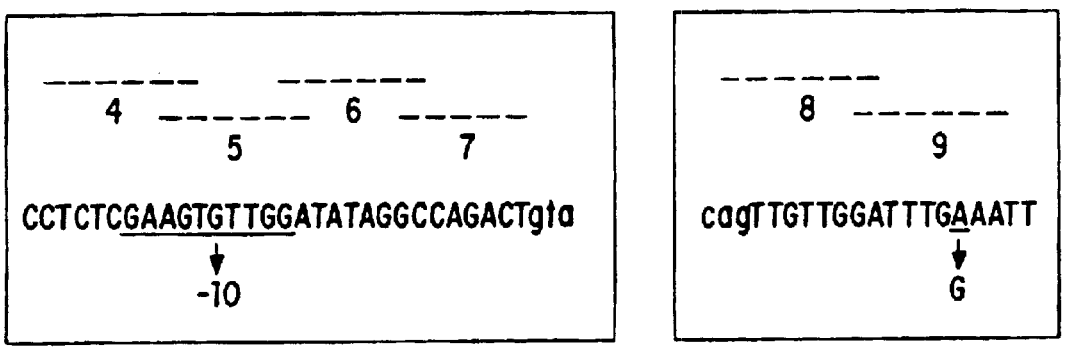
FIG. 5 provides an idealized schematic depiction of the results of an hprt mutation detection assay on a device in accordance with the present invention. The sequence depicted on the left side of the figure corresponds to nucleotides 23–55 of SEQ ID NO:2. One of the two sequences in the right side of the figure corresponds to nucleotides 3–22 of SEQ ID NO:4 (sequence with A in the 16th position from the left) and the other to nucleotides 3–22 of SEQ ID NO:5 (bottom sequence with G replacing A at position 16).
Figure 5:
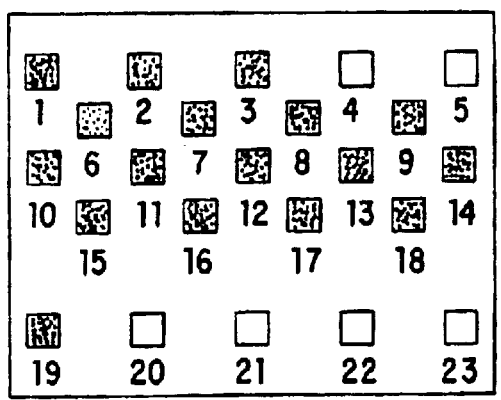
Figure 5:
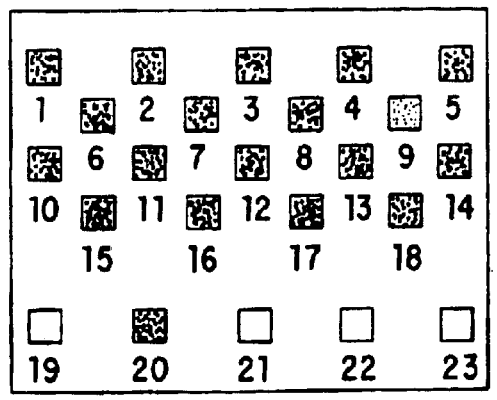

A high-density or ultra-high density microfabricated device according to the above examples is constructed and attachment of oligonucleotide probes is carried out within the bounded regions of the wafer. Included are the normal probes (1–18) plus the specific probes that correspond to five different known mutations, including the above mutations (sites 19 and 20, respectively). The foregoing uses two sets of PCR primers (Table I) to amplify the exons 7/8 region of hamster genomic DNA. A radioactive label ($^{32}$P) is incorporated into the PCR fragments during amplification, which enables detection of hybridization by autoradiography or phosphorimager. FIG. 5 illustrates the results when the above probes are attached at one end to the surface at specific test sites within the DNA chip (numbered as above). Idealized hybridization patterns for two of the mutants (10-base deletion on left and A-G transition on right) are shown at the bottom.

EXAMPLE 11

Profiling of Gene Expression Using cDNA Clones Arrayed in Porous Silicon

Part A: Fabrication of Porous Silicon Wafer

The procedure outlined in EXAMPLE 3 for fabrication of a porous silicon wafer with integral sample wells is followed, to yield a wafer with a 50×50 array of 200 $\mu$m square patches of pores, spaced 400 $\mu$m apart (center-to-center) over the surface of the wafer. The pores of the wafer are activated to bind amine-derivatized polynucleotides by reaction with epoxysilane, as described in EXAMPLE 4.

Part B: Formation of cDNA Array

A set of 2,500 M13 clones, selected from a normalized human cDNA library, is subjected to the polymerase chain reaction (PCR) in the presence of 5'-hexylamine-dUTP to amplify the cDNA inserts and incorporate primary amines into the strands. The PCR products are ethanol-precipitated, dissolved in water or 10 mM KOH, heat-denatured at 100° C. for 5 min., then quenched on ice and applied to individual sample wells of the porous wafer suing a Hamilton Micnolab 2200 fluid delivery system equipped with an 8-needle dispensing head. After all cDNA fragments are dispensed, a slight vacuum is briefly applied from below to ensure that fluid has occupied the pores. Following incubation at room temperature overnight or at 600C for 30–60 minutes, the porous wafer is flushed with warm water, then reacted with 50 mM triethylamnine to cap off the unreacted epoxy groups on the surface, then flushed again with warm water and air dried.

Part C: Preparation of Labeled PCR Fragments Representing the 3'-regions of Expressed Genes Cytoplasmic RNA is extracted from cultured cells by the method of Chomczynski and Sacchi (*Anal. Biochem.* 162:156–159 (1993)), treated with DNAse I to remove DNA contamination, then extracted with phenol/chloroform and ethanol precipitated. Reverse transcriptions and PCR are performed as described in the "differential display" protocol of Nishio et al. (*FASER J.* 8:103–106 (1994)). Prior to hybridization, PCR products are labeled by random priming in the presence of [A-$^{32}$P]dNTPs, and unincorporated label is removed by Centricon filtration.

Part D: Hybridization of Expressed Sequences to cDNA Array

Prior to hybridization, a solution of 1% "Blotto" or 50 mM tripolyphosphate is flowed through the porous silicon wafer to minimize the nonspecific binding of target DNA, then the porous silicon array is washed with hybridization solution (50 mM Tris-HCl, pH 7.5, 1 mM EDTA, 1M NaCl). Labeled PCR fragments representing the 3'-end of expressed genes are recovered from the Centricon filtration units in hybridization buffer, and the entire porous wafer is flooded with this DNA solution. The porous hybridization module is placed at 65° C. and a peristaltic pump, connected to the lower vacuum chamber, is used to gradually flow the labeled DNA through the pores of the wafer over the course of 30–60 minutes. The porous wafer is washed three times with hybridization buffer at 65° C.

Part E: Quantitation of Hybridization Signals

Following hybridization and washing, the porous wafer is briefly dried, then placed onto the phosphor screen of a phosphorimager and kept in the dark for a period of time determined by the intensity of label. The phosphor screen is then placed into the phosphorimager reader for quantitation of individual hybridization signals arising from each porous region in the array.

Figure 6:
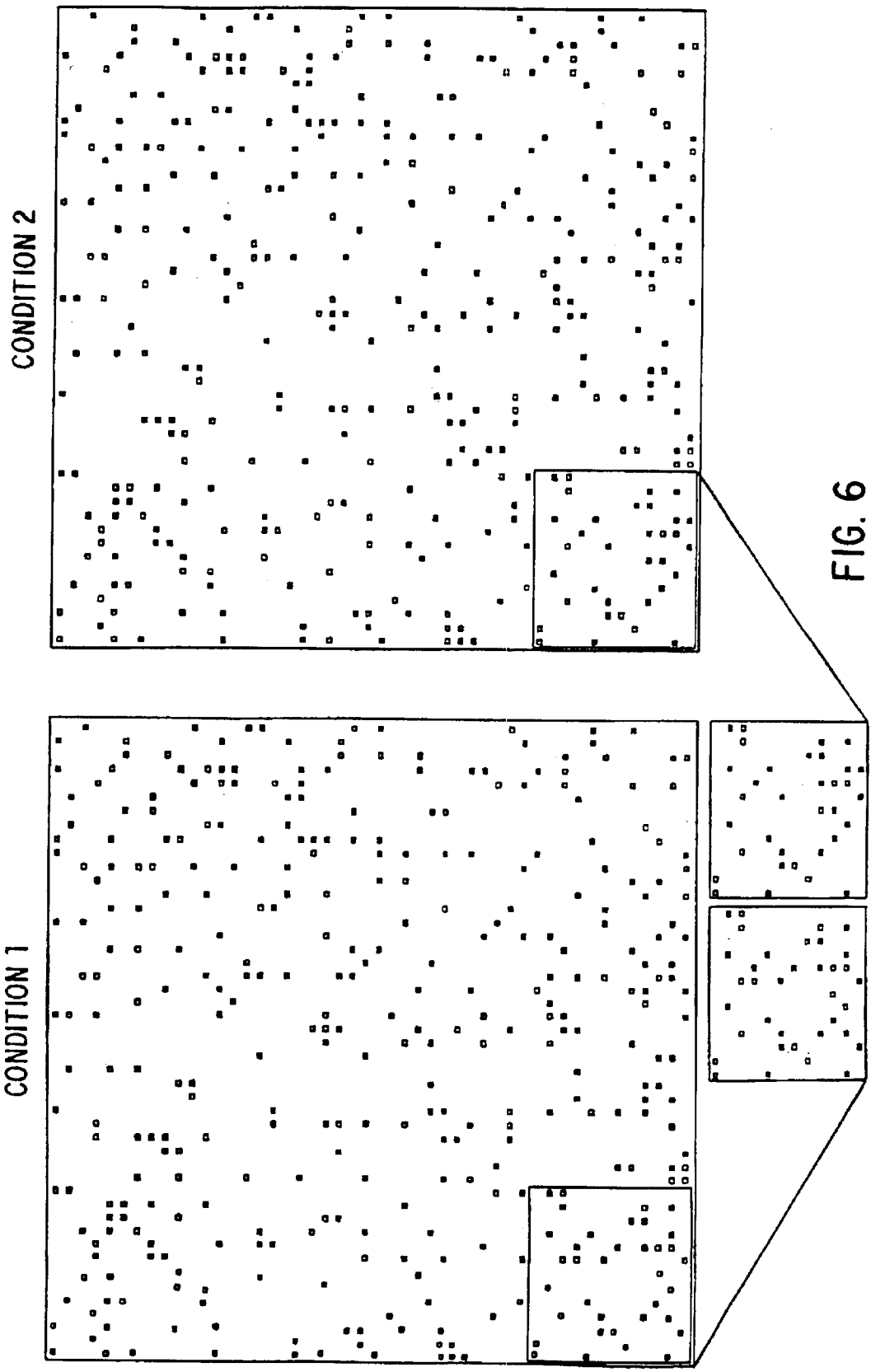
FIG. 6 provides an idealized schematic depiction of a hybridization assay performed to profile gene expression under different experimental conditions. Details of the assay procedure are provided in Example 11.

FIG. 6 illustrates results obtainable from a hybridization experiment. Total cytoplasmic mRNA is isolated from cells cultured under two conditions and subjected to the "differential display" procedure described above to prepare fragments representative of individual MRNA species present under the two conditions. These samples are hybridized to two identical cDNA arrays, to yield the two hybridization signal patterns shown. These patterns represent the profile of expressed genes under the two different culture conditions (for example in the presence and absence of a drug or chemical that induces a change in the expression of some genes). Note that overall, the pattern of hybridization is similar for the two conditions, but as expected for a diffential expression of certain genes under the two conditions, there are a few hybridization signals that are seen only for culture condition 1 and a few that are seen only for culture condition 2. The box in the lower left, reproduced at the bottom of the figure to assist visual comparison, represents several differences in the gene expression profile. The squares represent sites where hybridization has occurred and the darkness of the squares is proportional to the number of labeled fragments present at each site.

---

What is claimed is:

1. A method for detecting a binding reaction between a binding reagent and a binding target, comprising:
   (A) contacting a sample suspected of containing a binding target with a substrate comprised of: (i) oppositely facing first and second major surfaces, (ii) a multiplicity of discrete channels extending through said substrate from said first major surface to said second major surface, (iii) at least a first binding reagent immobilized on the walls of at least a first group of said channels and (iv) at least a second binding reagent immobilized on the walls of at least a second group of said channels; and
   (B) detecting binding between a binding target in the sample and at least one binding reagent on the walls of at least one group of discrete channels in the substrate, thereby detecting said binding reaction.

2. A method according to claim 1, wherein the first and second binding reagents differ from one another.

3. A method according to claim 1, wherein the first and second binding reagents bind different binding targets.

4. A method according to claim 1, wherein said substrate comprises groups of channels having areas of between about 20 $\mu m^2$ to about $3 \times 10^6$ $\mu m^2$.

5. A method according to claim 1, wherein there are between 400 and 4400 of said groups of discrete channels per $cm^2$ of cross-sectional area of the substrate.

6. A method according to claim 1 wherein a detectable label is used to detect the reaction.

7. A method according to claim 6, wherein said detectable label is selected from the group consisting of fluorescent, chemiluminescent and radioactive labels.

8. A method according to claim 7, wherein said detectable label is attached to said binding target.

* * * * *